US012594061B2

(12) United States Patent
Kanazawa et al.

(10) Patent No.: US 12,594,061 B2
(45) Date of Patent: Apr. 7, 2026

(54) URINALYSIS DEVICE AND HEALTH FACILITATION SYSTEM

(71) Applicant: FIRST SCREENING CO., LTD., Tokyo (JP)

(72) Inventors: Yohei Kanazawa, Tokyo (JP); Yoshito Tsunoda, Tokyo (JP)

(73) Assignee: FIRST SCREENING CO., LTD. (JP)

( * ) Notice: Subject to any disclaimer, the term of this patent is extended or adjusted under 35 U.S.C. 154(b) by 1092 days.

(21) Appl. No.: 17/442,187

(22) PCT Filed: Oct. 29, 2019

(86) PCT No.: PCT/JP2019/042409
§ 371 (c)(1),
(2) Date: Apr. 21, 2022

(87) PCT Pub. No.: WO2020/194830
PCT Pub. Date: Oct. 1, 2020

(65) Prior Publication Data
US 2022/0249068 A1 Aug. 11, 2022

(30) Foreign Application Priority Data

Mar. 26, 2019 (JP) ................................. 2019-057617

(51) Int. Cl.
*A61B 10/00* (2006.01)
*G01N 33/493* (2006.01)

(52) U.S. Cl.
CPC ......... *A61B 10/007* (2013.01); *G01N 33/493* (2013.01); *A61B 2503/40* (2013.01)

(58) Field of Classification Search
None
See application file for complete search history.

(56) References Cited

U.S. PATENT DOCUMENTS

2009/0123335 A1 5/2009 Nakamura et al.
2013/0144237 A1* 6/2013 Abraham ................ A61F 13/42
604/361

(Continued)

FOREIGN PATENT DOCUMENTS

JP 2005-172493 A 6/2005
JP 2006-042670 A 2/2006
(Continued)

OTHER PUBLICATIONS

International Search Report issued in PCT/JP2018/013645 (in English and Japanese), mailed Jul. 3, 2018; ISA/JP (total 8 pages).
(Continued)

*Primary Examiner* — Jennifer Robertson
*Assistant Examiner* — Om Patel
(74) *Attorney, Agent, or Firm* — Harness, Dickey & Pierce, P.L.C.

(57) ABSTRACT

A urinalysis device includes a target formed from a water-repellent material, an absorbent portion formed from a water-absorbing material and at least partially in contact with the target, a surface structure that forms a pathway for directing urine for application to the target; and a sensor element that is provided in the absorbent portion and outputs signals corresponding to components in the urine.

4 Claims, 13 Drawing Sheets

(56) References Cited

U.S. PATENT DOCUMENTS

| | | | |
|---|---|---|---|
| 2014/0121487 A1 | 5/2014 | Faybishenko | |
| 2014/0176913 A1 | 6/2014 | Wu | |
| 2015/0319486 A1 | 11/2015 | Wang | |
| 2015/0330958 A1 | 11/2015 | Carney | |
| 2016/0120473 A1 | 5/2016 | Linton et al. | |
| 2016/0345877 A1 | 12/2016 | Takeuchi et al. | |
| 2018/0104114 A1 | 4/2018 | Pepin | |
| 2018/0325743 A1 | 11/2018 | Ho | |
| 2019/0017994 A1 | 1/2019 | Tsuruoka et al. | |
| 2019/0069845 A1 * | 3/2019 | Wong | A61B 5/6808 |
| 2019/0254582 A1 | 8/2019 | Wei | |

FOREIGN PATENT DOCUMENTS

| | | | | |
|---|---|---|---|---|
| JP | 2007-121060 A | 5/2007 | | |
| JP | 2008-206592 A | 9/2008 | | |
| JP | 2010-054379 A | 3/2010 | | |
| JP | 2012-105839 A | 6/2012 | | |
| JP | 2016-214733 A | 12/2016 | | |
| JP | 6100447 B1 | 3/2017 | | |
| NL | 2013734 * | 8/2016 | | |
| WO | WO-0015108 A1 * | 3/2000 | | A61B 5/04087 |
| WO | 2003-001423 A1 | 1/2003 | | |
| WO | WO-2008002113 A1 * | 1/2008 | | A61B 10/007 |
| WO | WO-2017110161 A1 * | 6/2017 | | A01K 1/01 |
| WO | WO-2020126000 A1 * | 6/2020 | | A61B 5/053 |

OTHER PUBLICATIONS

Decision of Refusal by the JPO dated Sep. 29, 2020 (total 6 pages).
International Search Report (English and Japanese) of the International Searching Authority issued in PCT/JP2019/042409, mailed Jan. 21, 2020; ISA/JP (7 pages).

* cited by examiner

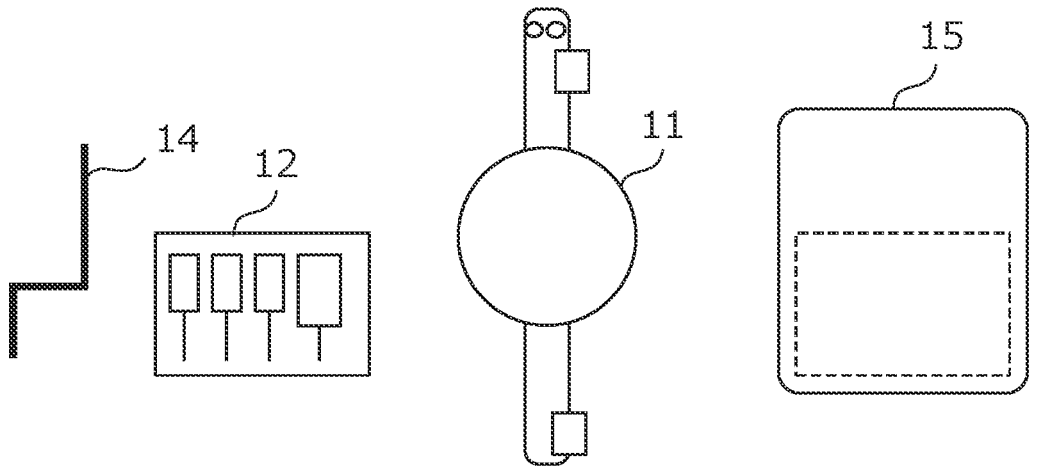
FIG. 3
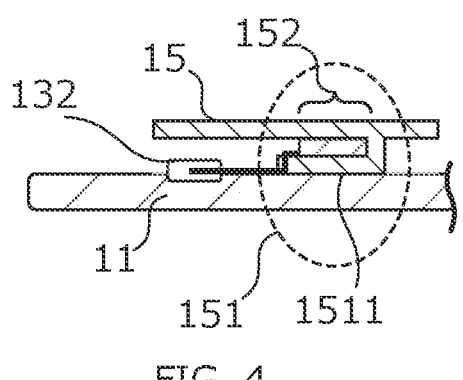
FIG. 4
FIG. 5A                    FIG. 5B
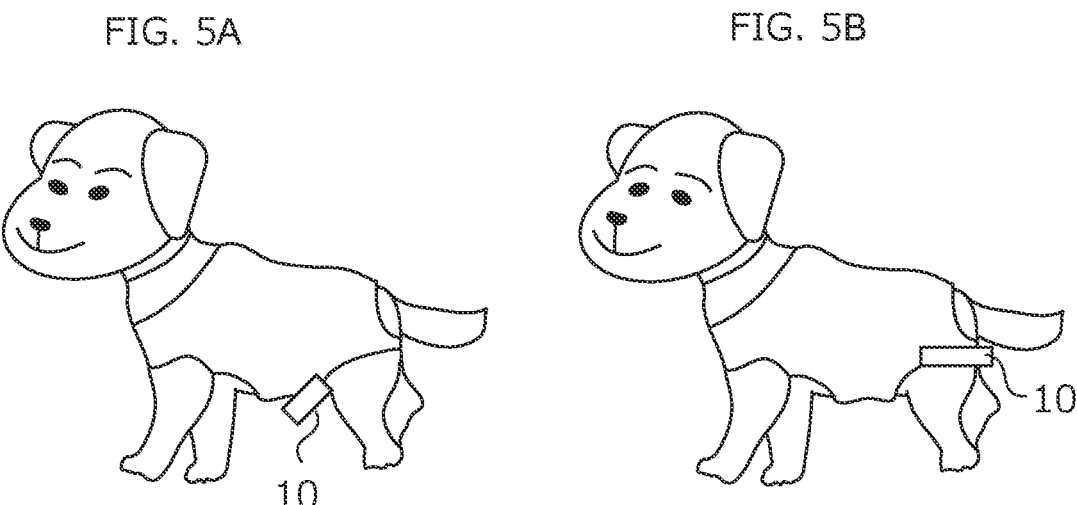

URINALYSIS DEVICE AND HEALTH FACILITATION SYSTEM

BACKGROUND

Technical Field

The present invention relates to a urinalysis device and a health support system.

Related Art

Systems for health care of pets and the like are known. For example, Patent Document 1 discloses a pet health management system for managing a health of a pet, including: a pet state information acquisition device for acquiring pet state information including at least information on one of body temperature, heart rate, respiration rate, step rate, exercise rate, action range, meal amount, stool amount, meal time, hydration amount, hydration time, position, and odor of the pet; and a pet health determination device for determining whether the pet is in a healthy state based on information included in the pet state information.

Prior Art Patent Document Reference

Patent Document 1: JP 2006-42670A

Problem to be Solved

In the technique described in Patent Document 1, only limited information such as body temperature, heart rate, respiration rate, step rate, exercise amount, movement range, meal amount, stool amount, mealtime, hydration amount, hydration time, position, and odor of the pet can be obtained. The present invention provides a technique for performing health care of a subject based on information obtained from urine.

SUMMARY

According to one aspect of the invention, there is provided a urinalysis device, comprising: a target formed from a water-repellent material; an absorbent portion formed from a water-absorbing material and at least partially in contact with the target; a surface structure that forms a pathway for directing urine for application to the target; and a sensor element that is provided in the absorbent portion and outputs signals corresponding to components in the urine.

The urinalysis device may further include a body having a longitudinal shape extending in one direction; a signal line that transmits an output signal from the sensor element; a connecting terminal that connects the signal line to an external device, wherein the absorbing portion, the sensor element, the signal line, and the connecting terminal are provided on the body, the absorbing portion is provided on one end side of the center in the longitudinal direction of the body, and the connecting terminal is provided on the other end side in the longitudinal direction of the body.

The urinalysis device may further include a body having a sheet shape, wherein the absorbing portion and the sensor element are provided in the body.

The urinalysis device may further include a box having an opening in at least a part other than the bottom surface, wherein the body is placed on the bottom surface, the bottom surface being inclined such that, in the installed state of the body, a part corresponding to the absorbing portion is low and a part corresponding to the target is high.

The urinalysis device may further include a support plate fixed to the upper side of the body in the box and having at least one through-hole formed therein.

The box and the support board may be formed from of paper.

The urinalysis device may further include a body on which the absorbing part and the sensor element are formed, and a fixing part for detachably fixing the body to a pet harness.

The fixing part may be selectively attachable to and detachable from a first position in which the body is located forward of a rear foot of a pet in a use state, and a second position in which the body is located rearward of the rear foot of the pet.

The fixing part may include a signal line that transmits a signal output from the sensor element, and a connecting terminal that connects the signal line to an external device.

According to another aspect of the invention, there is provided a health support system including: the urinalysis device; a transmitter connected to the sensor element; and a user terminal used by the user, wherein the transmitter includes an input unit to which an output signal of the sensor element is input, a storage unit that stores an identifier of the transmitter, and a wireless communication unit that transmits data corresponding to the output signal and a wireless signal indicating the identifier, the user terminal includes, a storage unit that stores an identifier corresponding to the user, a wireless receiving unit that receives the wireless signal from the transmitter, an output unit for outputting the data to an analyzing system that analyzes a health condition of the user based on a specific component indicated by the data when the identifier indicated by the radio signal matches the identifier stored in the storage unit, and an obtaining unit that obtains information corresponding to the result of the analysis from the analyzing system.

BRIEF DESCRIPTION OF THE DRAWINGS

FIG. 3 is an exploded view of urine sensor 10.

FIG. 4 is a diagram illustrating a cross-sectional structure of urine sensor 10.

FIGS. 5A and 5B are diagrams showing another example of the configuration of urine sensor 10.

DETAILED DESCRIPTION

1. First Embodiment 1-1. Configuration

Figure 1:
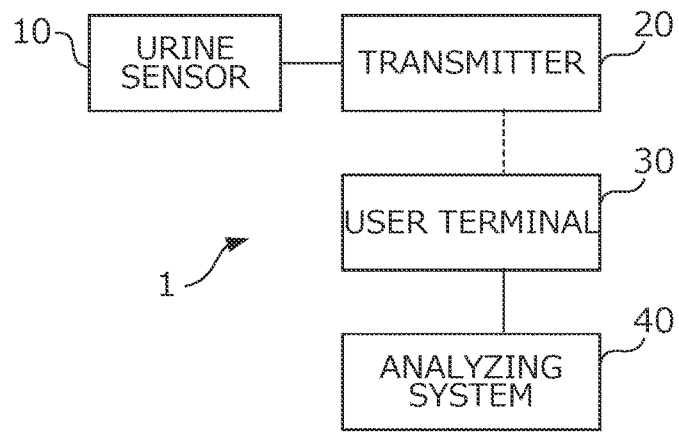
FIG. 1 is a diagram showing an outline of a health support system 1 according to a first embodiment.

FIG. 1 is a diagram showing in outline a health support system 1 according to the first embodiment. Health support system 1 is a system that detects specific components in urine of a subject and uses the detection results to provide information for health support of the subject. The subject referred to herein is an animal, and may include pets, domestic animals, and humans. Health support system 1 includes urine sensor 10, transmitter 20, user terminal 30, and analyzing system 40. Urine sensor 10 detects specific components in urine. Transmitter 20 transmits to user terminal 30 detection results obtained by urine sensor 10. User terminal 30 receives the detection results from transmitter 20, and transmits to analyzing system 40 the detection results. Based on the detection results, analyzing system 40 analyzes a health condition of the subject. Analyzing system 40 transmits to user terminal 30 information corresponding to the analysis result. User terminal 30 provides information corresponding to the analysis result to a user who is an animal administrator. In FIG. 1, urine sensor 10, transmitter 20, and user terminal 30 are each shown singly, but health support system 1 may have a plurality of at least one of these.

1-1-1. Urine Sensor 10

Figure 2:
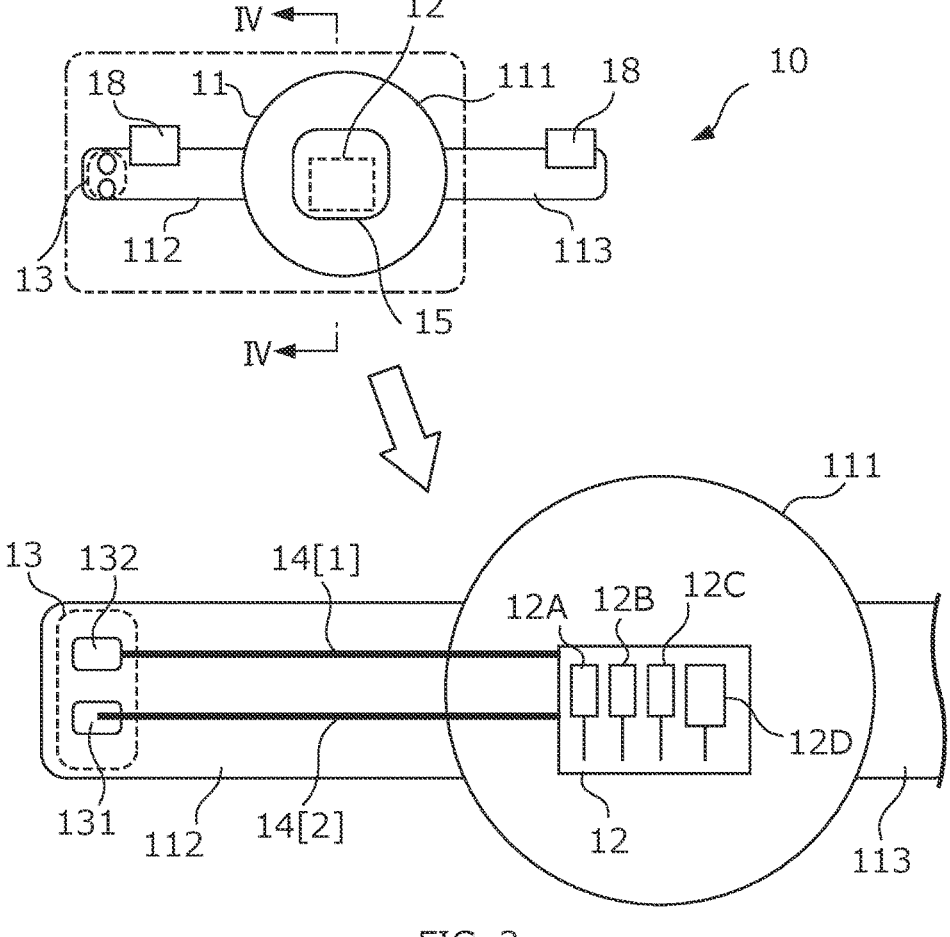
FIG. 2 is a diagram showing an example of the configuration of urine sensor 10.

FIG. 2 is a diagram showing an example of a configuration of urine sensor 10. Urine sensor 10 is an example of a urinalysis device, and includes a base 11, a sensor element 12, a detachable mechanism 13, and a detachable mechanism 18. Base 11 is a member for securing a mechanical strength and a size of urine sensor 10 that is easy to handle. Sensor element 12 outputs a signal corresponding to a specific component in urine. As sensor element 12, for example, a biosensor using an enzyme or a sensor using a diamond electrode is used. As a biosensor using an enzyme, for example, the sensor described in the paper by Nakamura et al. (Hideaki Nakamura, Yosuke Tsuboi and Masao Gotoh, "A simple potentiometric urine glucose biosensor using a paper-based disposable reagent sheet and a mobile pH meter," Current Topics in Analytical Chemistry, 9, pp. 71-75 (2012)) can be referred to. As a sensor using a diamond electrode, for example, a sensor described in Ogata et al. (G. Ogata, Y. Ishii, K. Asai, Y. Sano, F. Nin, T. Yoshida, T. Higuchi, S. Sawamura, T. Ota, K. Hori, K. Maeda, S. Komune, K. Doi, M. Takai, I. Findlay, H. Kusuhara, Y. Einaga, H. Hibino, "A microsensing system for the in vivo real-time detection of local drug kinetics," Nature Biomed OOD., 1, 654-666 (2017)) can referred to.

Sensor element 12 is attached to base 11. In this example, plural sensor elements 12 are attached to base 11. The plural sensor elements 12 are each responsive to a different component in urine. In one embodiment, urine sensor 10 includes four sensor elements 12A, 12B, 12C and 12D. Sensor element 12A measures urine pH, sensor element 12B measures urine uric acid, sensor element 12C measures urine oxalate, and sensor element 12D measures urine glucose. Since the pH represents a concentration of hydrogen ions in urine, a detection result of a "specific component in urine" is represented.

Detachable mechanism 13 is a mechanism for detachably fixing base 11 to transmitter 20. Detachable mechanism 13 forms a transmission path that transmits the output signal from sensor element 12. Detachable mechanism 13 is at least partially formed from a conductive material, and the output signal is transmitted through the conductive material.

Base 11 includes circular member 111, belt-shaped member 112, and belt-shaped member 113. In this example, circular member 111 has a circular shape and is an example of a "target" by which the subject applies urine to the sensor element. Here, an area of the portion exposed on the surface is larger than that of the absorption portion, described later. Belt member 112 and belt member 113 have a band-like shape. Belt member 112 and belt member 113 are each fixed to circular member 111. Circular member 111, belt member 112, and belt member 113 are formed from a water-repellent material. Circular member 111, belt member 112, and belt member 113 are each formed from a combustible material, examples of which include cloth or paper.

Snap fitment 131 and snap fitment 132 are formed on base 11. Snap fitment 131 and snap fitment 132 are examples of detachable mechanism 13. Wiring 14 is formed on base 11, and transmits an output signal from sensor element 12 to the detachable mechanism 13 (for example, snap fitment 131 and snap fitment 132). For one sensor element 12, one set of wires (that is, two wires) 14 is used. When distinguishing the two wires, they are referred to as wiring 14[1] and wiring 14[2]. Sensor element 12 is connected to wiring 14[1] and wiring 14[2] and outputs an output signal corresponding to a specific component in the urine. If urine sensor 10 has k sensor elements 12, where k is a natural number greater than or equal to 2, then k sets of wires 14 are used. When outputting a signal from k pieces of sensor element 12 in space division, the detachable mechanism 13, for example, has 2 k lines 14 and 2 k snap fitments. For simplification in the drawings, only two wires 14 and two snap fitments are shown.

Urine sensor 10 further includes sheet 15 for covering sensor element 12. Sheet 15 (an example of an absorbent portion) is formed from a water-absorbing material, and at least a part thereof is in contact with base 11. Sheet 15 is formed from a material that is softer than base 11, specifically, is a material having a stiffness that is less than that of base 11.

FIG. 3 is an exploded view of urine sensor 10. Urine sensor 10 consists of base 11, which includes detachable mechanism 13 and detachable mechanism 18, sensor element 12, wiring 14, and sheet 15. In this example, urine sensor 10 is disposable. When the subject animal urinates, the animal's urine is applied to the surface of urine sensor 10 covered by sheet 15. The urine passes through sheet 15 and reaches sensor element 12. Sensor element 12 measures specific components in the urine. After measurement, the animal owner peels sheet 15 from base 11. The animal owner flushes sheet 15 down a toilet, and folds base 11 and discards it in a trash bin. An adhesive layer (not shown in the figures) for folding base 11 is formed on the back surface of base 11 to which sensor element 12 is attached. On a surface of sheet 15 facing base 11, a protective film (not shown in the figures) is adhered to a region that is provided with an adhesive layer. In a state in which sheet 15 is attached to base 11, the adhesive layer is covered with a protective film and the surface is not exposed. When sheet 15 is peeled from base 11, the protective film peels off from the adhesive layer, and the adhesive layer is exposed. It is of note that this is an example of a disposal method, and in reality, urine sensor 10 is sorted in accordance with local laws and the like applicable to the environment in which it is used.

FIG. 4 is a diagram illustrating a cross-sectional structure of urine sensor 10. FIG. 4 is a view showing a cross-section through the center of base 11 as viewed from the front of base 11, which is the IV-IV cross-section in FIG. 2. In this example, sheet 15 is provided with pocket 151 on a side surface of base 11. Sensor element 12 is housed in pocket 151. Surface 1151 of pocket 151 on the side of base 11 is adhered to base 11 by use of, for example, an adhesive. On the surface of circular member 111, a surface structure is formed that serves as a path for guiding the urine applied to circular member 111 to sheet 15. Here, the surface structure refers to a three-dimensional shape of the surface of circular member 111 in the use state of urine sensor 10, and refers to, for example, a concave portion, a convex portion, an inclined portion, or a combination thereof. In one example, circular member 111 has a funnel-like shape with a perimeter that is higher than the center. The urine applied to the periphery descends under gravity to the center due to the difference in height. Sheet 15 is provided at the center. Sensor element 12 is provided on sheet 15. Region 152 covering sensor element 12 of sheet 15 is thinner than the other regions. As a result, urine is able to reach sensor element 12 with comparative ease. Sheet 15 is perforated around pocket 151 so that portions other than pocket 151 can be separated and discarded.

In this example, urine sensor 10 is not provided with a power source (battery) and operates by receiving power from another device (in this example, from transmitter 20).

In this example, base 11 has a sheet-shaped body; and circular member 111 (an example of a target), sheet 15 (an example of an absorbing portion), and sensor element 12 are provided on base 11.

Detachable mechanism 18 is a fixing part for detachably fixing urine sensor 10, which is a main body on which sheet 15 and sensor element 12 are formed, to a harness or clothing for pets or the like. Detachable mechanism 18 is, for example, a hook and loop fastener.

Detachable mechanism 18 is selectively attachable/detachable to/from a first position in which the body of urine sensor 10 is located forward of the rear foot of the pet, and a second position in which the body is located rearward of the rear foot of the pet in the use state.

FIGS. 5A and 5B are diagrams illustrating a state in which urine sensor 10 is fixed to a clothing of a pet dog, as an example of a pet harness. In the example shown in FIGS. 5A and 5B, urine sensor 10 is fixed by the detachable mechanism 18 at a position where urine is applied to sheet 15 when the pet urinates. FIG. 5A is a diagram illustrating the fixing position of urine sensor 10 when the pet is a male dog, and FIG. 5B is a diagram illustrating the fixing position of urine sensor 10 when the pet is a female dog. In the example (a), detachable mechanism 18 is fixed to a portion (an example of the first position) in which the body of urine sensor 10 is located at the front side of the rear foot of the pet in the use state of urine sensor 10. On the other hand, in the example (b), the detachable mechanism 18 is fixed to a portion (an example of the second position) in which the main body of urine sensor 10 is positioned behind the rear foot of the pet in the use state of urine sensor 10.

Figure 6:
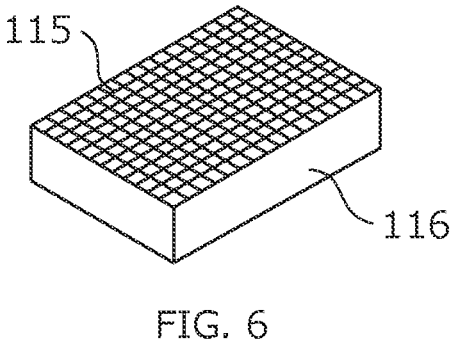
FIG. 6 is a diagram showing another example of the configuration of urine sensor 10.
Figure 7:
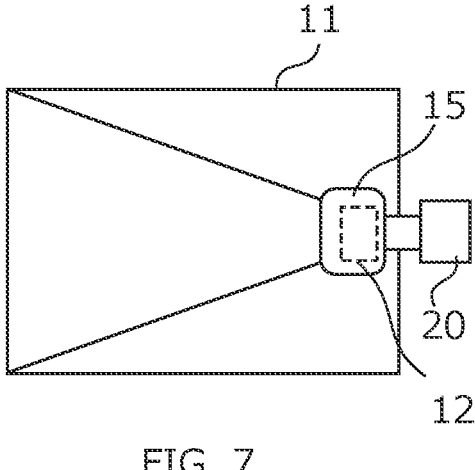
FIG. 7 is a diagram showing another example of the configuration of urine sensor 10.
Figure 8:
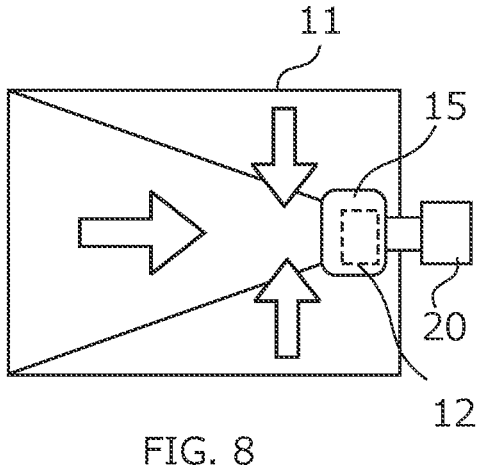
FIG. 8 is a diagram showing another example of the configuration of urine sensor 10.

FIGS. 6 to 8 are diagrams showing another example of the configuration of urine sensor 10. Urine sensor 10 illustrated in FIGS. 2-4 is mounted at a position where the pet was exposed to urine when urinating. In the examples shown in FIGS. 6 to 8, base 11 acts as a toilet seat for pets. Base 11 (an example of a target) is formed from a water-repellent material.

FIG. 6 is a perspective view showing the external appearance of urine sensor 10, and FIG. 7 is a top view of urine sensor 10. In the example shown in FIG. 7, base 11, which is a toilet sheet, is installed on the bottom surface of box 116, which is a pet toilet. At least a part of box 116 other than the bottom surface is open. In box 116, support plate 115 is fixed to an upper portion of base 11. Support plate 115 is a member in which at least one through-hole is formed. Box 116 and support plate 115 are formed from, for example, paper.

Sheet 15 and sensor element 12 are attached to the end portion of base 11. Sheet 15 is formed from a water-absorbing material, and at least a portion thereof is in contact with base 11. Sheet 15 is an example of an absorbing portion. Sheet 15 and sensor element 12 are fixed to base 11 by a detachable mechanism such as a hook and loop fastener, for example. The bottom surface of box 116 is inclined toward sheet 15 at a portion of base 11 such that a portion corresponding to the target where the pet urinates in the state where base 11 is installed is high and a portion corresponding to sheet 15 (a portion where sheet 15 is installed) is relatively low. The inclined structure may be included in base 11, for example, and the thickness of the base material varies depending on its position. Alternatively, the inclined structure may be formed on the bottom surface of box 116 accommodating base 11, and base 11 may be flat.

FIG. 8 is a view exemplifying a direction of inclination of base 11. In the example in FIG. 8, urine moves in the direction indicated by the arrow in the figure due to the inclination of base 11. As described above, base 11 has a surface structure that forms a path for guiding urine applied to base 11 to sheet 15. Sensor element 12 is provided on sheet 15. When the pet urinates on base 11, urine moves down the inclination to the position of sensor element 12, touches sensor element 12, and sensor element 12 outputs a signal indicating detection results of specific components.

In this example, base 11 has a sheet-shaped body, and a surface that is water repellent and is an example of a target. Sheet 15 (an example of an absorbing portion), and sensor element 12 are provided on base 11.

1-1-2. Transmitter 20

Figure 9:
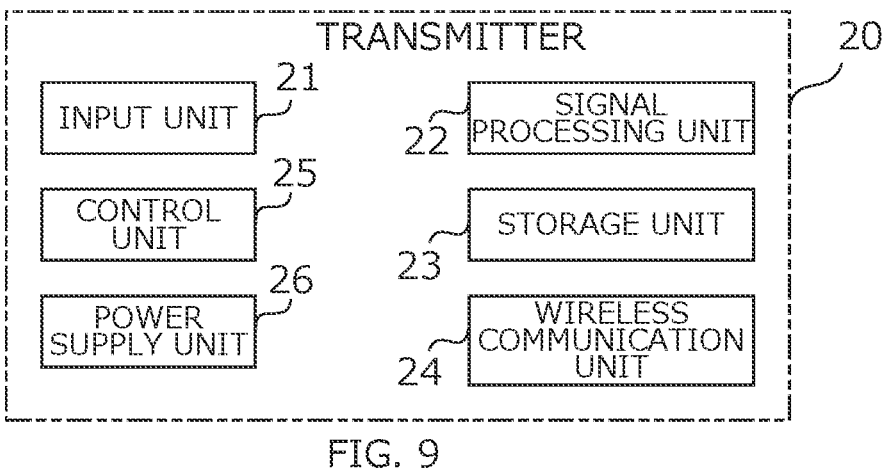
FIG. 9 is a diagram illustrating a configuration of a transmitter 20.

FIG. 9 is a diagram illustrating a functional configuration of transmitter 20. Transmitter 20 is a device that transmits information detected by urine sensor 10 to user terminal 30. While urine sensor 10 is disposable, transmitter 20 can be used repeatedly.

Transmitter 20 has input unit 21, signal processing unit 22, storage unit 23, wireless communication unit 24, control unit 25, and power supply unit 26. Input unit 21 receives an input of an output signal from urine sensor 10. Signal processing unit 22 performs a variety of signal processing. The processing performed by signal processing unit 22 includes, for example, a process of storing a signal received as data by input unit 21 in storage unit 23. Storage unit 23 stores a variety of data. Wireless communication unit 24 performs wireless communication with another device in accordance with a predetermined communication protocol. The communication protocol is, for example, IEEE 802 15.1, i.e., so-called Bluetooth (registered trademark). Control unit 25 controls other elements of transmitter 20. Power supply unit 26 is an example of a power supply unit for supplying power for use in operating transmitter 20 and urine sensor 10.

Figure 10:
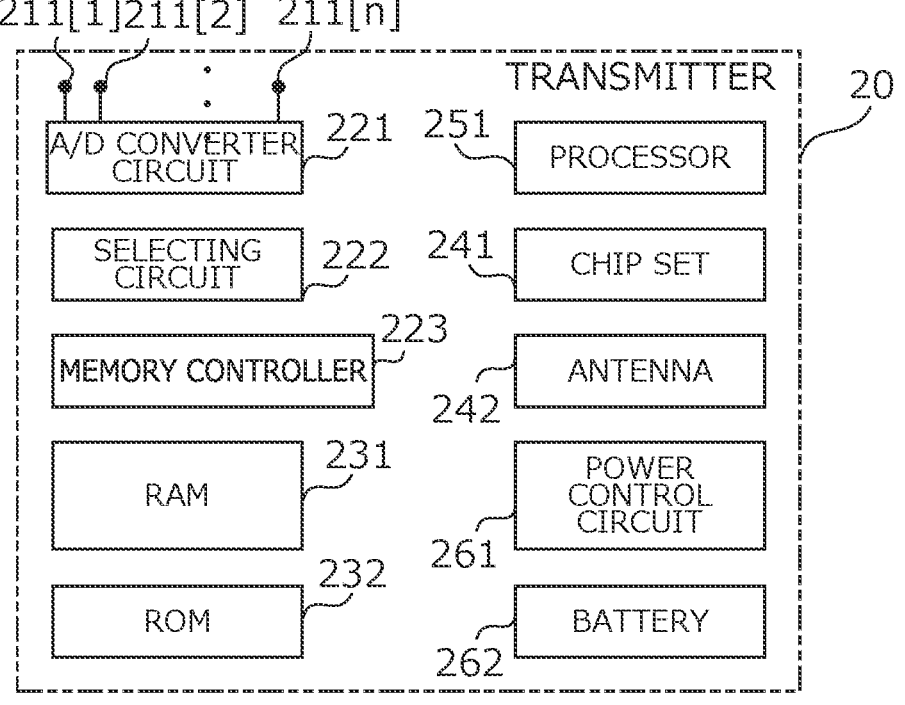
FIG. 10 is a diagram illustrating a hardware configuration of transmitter 20.

FIG. 10 is a diagram illustrating a hardware configuration of transmitter 20. Transmitter 20 has n input terminals (including first terminal 211[1] and second terminal 211[2]), A/D converter circuit 221, selecting circuit 222, memory controller 223, RAM 231, ROM 232, chip set 241, antenna 242, processor 251, power control circuit 261, and battery 262. The input terminal of the plurality (n≥2) including first terminal 211[1], second terminal 211[2], . . . and the n-th terminal 211[n] is a terminal for use where urine sensor 10 has a plurality of sensor elements 12. Transmitter 20 corresponds to a urine sensor 10 having a maximum of n sensor elements 12. The signal input via the k-th terminal 211[k] is referred to as a signal S[k]. k is a natural number that satisfies 1≤k≤n. A/D converter circuit 221 converts the signal input via the input terminals (analog signal) to a digital signal. Selecting circuit 222 selects one signal from the n input signals, and outputs the selected signal. In this example, selecting circuit 222 repeatedly selects in order one signal from the n input signals. Specifically, after the signals S[1], S[2], S[n] and the signals S[1] to S[n] are selected in order, the signals S[1] to S[n] are again selected in order. That is, selecting circuit 222 selects the S [n] from the signal S [1] in time division. Memory controller 223 writes data into RAM 231 in accordance with signals outputted from selection circuits 222. Data obtained by converting an output signal from urine sensor 10 is referred to as measurement data.

Figure 11:
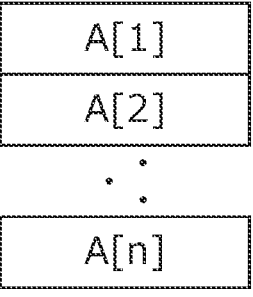
FIG. 11 is a diagram illustrating a storage area for measurement data.

FIG. 11 is a diagram illustrating a storage area of measurement data. In RAM 231, the storage area for the measured data is divided into n pieces (storage area A[1] to A[n]). The number of segments of the storage area is equal to the number of input terminals (the number of largest sensor elements 12 that can be supported). The storage area A[k] stores data of the signal S[k]. Each storage area stores latest measurement data.

Referring again to FIG. 10, RAM 231 is a volatile memory device that stores measured data and other data. ROM 232 is a non-volatile memory device that stores a program or the like executed by processor 251. In this instance, ROM 232 stores data indicating identifiers for identifying each of the plurality of transmitters 20. Hereinafter, this data is referred to as "identifier data," and the identifier of transmitter 20 is referred to as "transmitter identifier." This identifier allows each transmitter 20 to be distinguished even when multiple transmitters 20 are used in health support system 1. Chipset 241 and antenna 242 are circuit groups and antennas for carrying out wireless communication in accordance with the communication protocols described above. Processor 251 is a microcontroller for controlling other elements of transmitter 20. Battery 262 is a battery for supplying electric power for driving transmitter 20 and urine sensor 10, and may either be a primary battery or a secondary battery. Power control circuit 261 is a circuit for controlling on-off of the power supply of transmitter 20.

In this embodiment, processor 251 sequentially specifies one storage area from among a plurality of storage areas for the measurement data in RAM 231, and reads the measurement data from the designated storage area. Processor 251 adds an identifier for the storage area to the measurement data. Since the storage area and sensor element 12 have a one-to-one correspondence as described with reference to FIG. 11, the identifier of the storage area corresponds to the identifier of sensor element 12, as will be described later. Processor 251 controls chipset 241 to transmit a pair of measurement data and storage area identifiers.

With respect to the relationship between FIG. 9 and FIG. 10, first terminal 211 and the second terminal 212 are an example of input unit 21. A/D conversion circuit 221, selecting circuit 222, and memory controller 223 are an example of a signal processing unit 22. RAM 231 and ROM 232 are an example of storage unit 23. Chipset 241 and antenna 242 are an example of a wireless communication unit 24. Processor 251 is an example of control unit 25. Power control circuit 261 and battery 262 are an example of a power supply unit 26.

Figure 12:
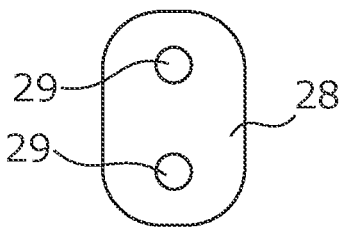
FIG. 12 is a diagram illustrating an external appearance of transmitter 20.

FIG. 12 is a diagram illustrating an appearance of transmitter 20. In this example, transmitter 20 has housing 28 and detachable mechanism 29. Housing 28 is a housing for protecting elements such as processor 251, and for facilitating handling. Housing 28 may have a structure in which at least a part thereof can be opened and closed for replacement of battery 262. The detachable mechanism 29 is a mechanism for detaching urine sensor 10 from detachable mechanism 13, and is, for example, a snap fitment.

1-1-3. User Terminal 30

Figure 13:
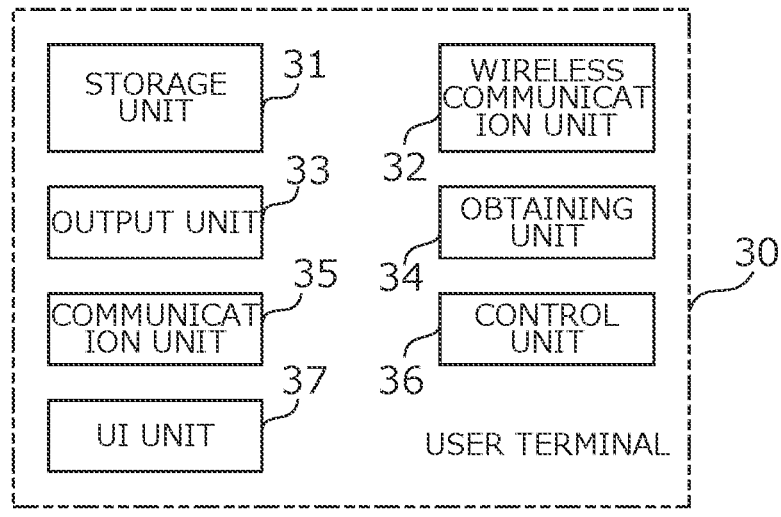
FIG. 13 is a diagram illustrating a functional configuration of user terminal 30.

FIG. 13 is a diagram illustrating a functional configuration of user terminal 30. User terminal 30 receives measurement data from transmitter 20, and further displays information obtained by analyzing the measurement data. User terminal 30 is carried by a user who is the owner of the pet using urine sensor 10.

User terminal 30 includes storage unit 31, wireless communication unit 32, output unit 33, obtaining unit 34, communication unit 35, control unit 36, and UI unit 37. Storage unit 31 stores a variety of data. The data stored in storage unit 31 includes an identifier (hereinafter, referred to as "user identifier") that specifies a user of user terminal 30. Further, the data stored in storage unit 31 includes information for specifying a pair of a user identifier and a transmitter identifier. In the present embodiment, transmitter 20 is not shared by an unspecified number of users, but is dedicated to a specific single or small number of users. The number of users using a certain transmitter 20 is limited. The user obtains the transmitter identifier of transmitter 20 used by the user by an appropriate known method, and stores the transmitter identifier in storage unit 31 in association with the user identifier of the user.

Wireless communication unit 32 is an example of a wireless receiving unit that receives a wireless signal from transmitter 20. Wireless communication unit 32 complies with the same communication protocol (e.g., Bluetooth (registered trademark)) as wireless communication unit 24 of transmitter 20. If the identifiers indicated by the received wireless signal and the identifiers stored in storage unit 31 match, that is, if a transmitter identifier received from the transmitter 20 and the transmitter identifier stored in conjunction with the user identifier in storage unit 31 match, output unit 33 outputs the measurement data received from the transmitter 20, to analyzing system 40. The reason why the coincidence of the transmitter identifier is confirmed here is to exclude data transmitted from transmitter 20 used by other users. If the transmitter identifier received from transmitter 20 does not match the transmitter identifier stored in storage unit 31 in association with the user identifier, the control unit 36 may delete the measurement data from storage unit 31. Obtaining unit 34 obtains information corresponding to the result of analysis using the measurement data from analyzing system 40. The information corresponding to the analysis result may be information indicating the analysis result itself of the measurement data, or may be information obtained using the analysis result.

Communication unit 35 performs communication according to a predetermined communication protocol. The communication protocol used by communication unit 35 is different from that used by wireless communication unit 32, as an example, a mobile communication protocol such as LTE (Long Term Evolution) or a wireless LAN protocol such as Wi-Fi. The control unit 36 controls other elements of user terminal 30. UI unit 37 provides a UI for the user of user terminal 30. UI unit 37 functions as a receiving unit that receives an input of an instruction or information from a user, and as an output unit that outputs a variety of types of information to the user. The output unit includes a display unit for visually outputting the variety of types of information.

Figure 14:
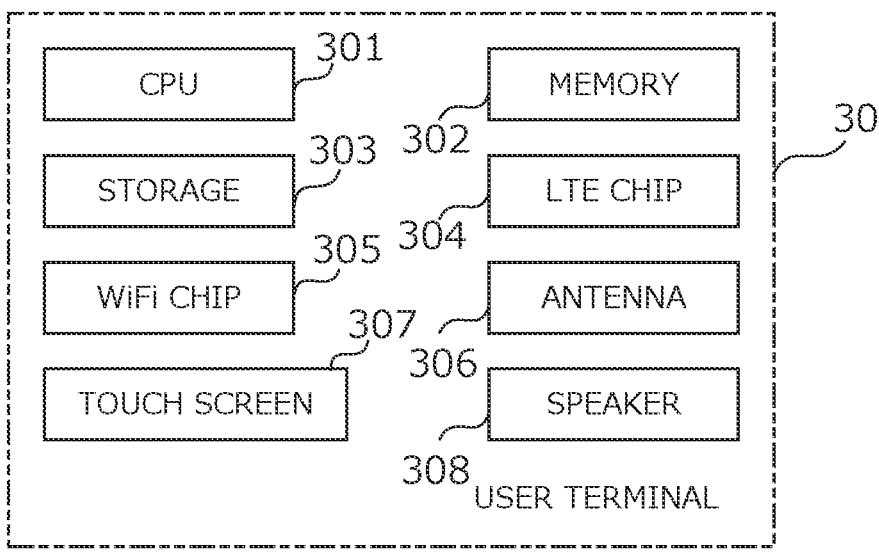
FIG. 14 is a diagram illustrating a hardware configuration of user terminal 30.

FIG. 14 is a diagram illustrating a hardware configuration of user terminal 30. User terminal 30 is a computer device, e.g., a smart phone, having CPU 301, memory 302, storage 303, LTE chips 304, WiFi chip 305, antenna 306, touch screen 307, and speaker 308. CPU 301 is a device that performs a variety of operations in accordance with a program and controls other hardware elements. Memory 302 is a main storage device that stores a variety of data. Storage 303 is a device that stores a variety of data and programs. LTE chip 304 is a chipset that communicates in accordance with the LTE protocol. WiFi chip 305 is a chip set for communication in accordance with WiFi protocol. Antenna 306 is an antenna that transmits and receives radio waves, for LTE chip 304 and WiFi chip 305. Touch screen 307 is an input/output device equipped with a display for displaying information, and a touch sensor provided on a screen of the display device. Speaker 308 is a sound output device.

In this example, storage 303 stores a program (hereinafter, referred to as "client program") for causing the computer device to function as user terminal 30. When CPU 301 executes the client program, the functions shown in FIG. 13 are implemented in the computer device. Upon execution of the client program by CPU 301, memory 302 and storage 303 are examples of storage unit 31. WiFi chip 305 and the antenna 306 are an example of a wireless communication unit 32. CPU 301 is examples of an output unit 33, obtaining unit 34, and control unit 36. LTE chip 304 and the antenna 306 are an example of communication unit 35.

1-1-4. Analyzing System 40

Figure 15:
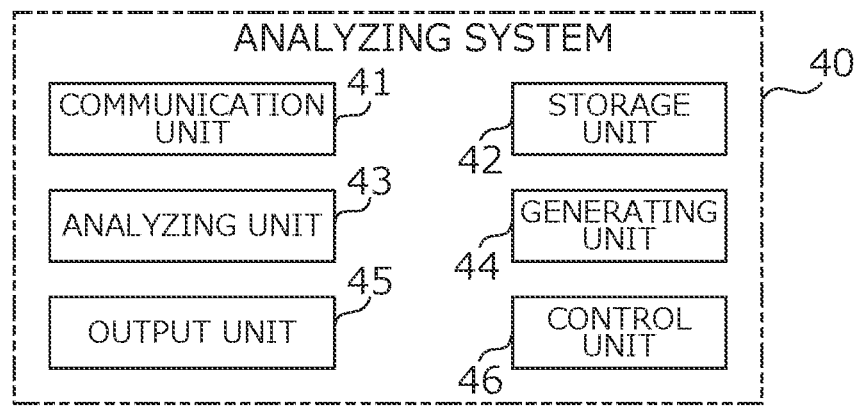
FIG. 15 is a diagram illustrating a functional configuration of analyzing system 40.

FIG. 15 is a diagram illustrating a functional configuration of analyzing system 40. Analyzing system 40 analyzes the health state of the user using the measurement data output from user terminal 30. Analyzing system 40 may be implemented in a device that is physically separate from user terminal 30, such as a so-called cloud, or may be implemented in the same device as user terminal 30. By implementing analyzing system 40 in, for example, a cloud, an effect of reducing a load on user terminal 30 and an effect of statistically processing the measurement data relating to a plurality of users can be achieved. By implementing analyzing system 40 in the same device as user terminal 30, user terminal 30 can be used in a stand-alone manner, and privacy of the measurement data can be maintained. Here, an example in which analyzing system 40 is implemented in a cloud is used.

Analyzing system 40 includes communication unit 41, storage unit 42, analyzing unit 43, generating unit 44, output unit 45, and control unit 46. Communication unit 41 communicates with user terminal 30. Storage unit 42 stores a variety of data. In this example, the data stored in storage unit 42 includes data in which the detection result (measurement data) of the specific component in the urine is recorded in time series (hereinafter referred to as "time-series data"). Storage unit 42 stores time-series data or each of the plurality of users. Analyzing unit 43 analyses a health state of the user using the time-series data. The analysis of the health state is performed in accordance with a predetermined algorithm. AI (Artificial Intelligence) technologies such as deep learning may be used for analysis of health conditions. Generating unit 44 generates information related to the analysis result in analyzing unit 43. The related information includes, for example, at least one of the following (1) to (4):

(1) Information directly indicating analysis results (e.g., visualization of time-series data as a graph);

(2) Information obtained by interpreting the analysis result (e.g., information for presenting diseases inferred from time-series data);

(3) Advice based on the results of the analysis (e.g., a diet menu or exercise menu suitable for diabetes for a user who has been analyzed as likely to have diabetes); and (4) Recommendations for commodities associated with analysis results (e.g., recommendations for beverages using green leafy vegetables (e.g., kale) for users with a low pH (acidic).

The above-mentioned related information is an example of information corresponding to analysis results of measurement data. Output unit 45 outputs to user terminal 30 data indicating related information (hereinafter referred to as "related information data"). Control means 46 performs a variety of controls.

Figure 16:
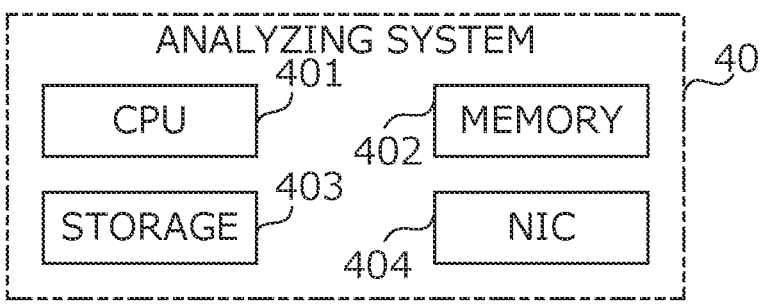
FIG. 16 is a diagram illustrating a hardware configuration of analyzing system 40.

FIG. 16 is a diagram illustrating a hardware configuration of analyzing system 40. Analyzing system 40 is a computer device having CPU 401, memory 402, storage 403, and NIC (Network Interface Controller) 404, such as a server device on the Internet. CPU 401 is a device that performs a variety of operations in accordance with a program, and controls other hardware elements. Memory 402 is a main storage device that stores a variety of data. Storage 403 is a device that stores a variety of data and programs. NIC 404 is a device that communicates in accordance with a predetermined communication protocol (e.g., Ethernet (registered trademark)).

In this example, storage 403 stores a program (hereinafter, referred to as "analysis program") for causing the computer device to function as analyzing system 40. Upon execution of CPU 401 the analysis program, NIC 404 is an example of communication unit 41. Memory 402 and storage 403 are examples of storage unit 42. CPU 401 are an example of analyzing unit 43, generating unit 44, output unit 45, and control unit 46.

1-2. Operation

Figure 17:
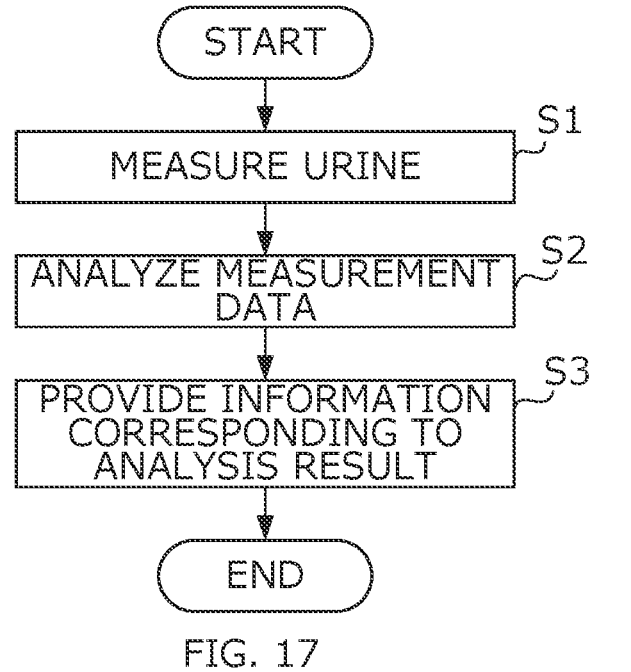
FIG. 17 is a diagram illustrating an outline of an operation of health support system 1.

FIG. 17 is a diagram illustrating an outline of the operation of health support system 1. At step S1, health support system 1 measures urine of a pet. At step S2, health support system 1 analyzes the measurement data. At step S3, health support system 1 provides information corresponding to the analysis result of the measurement data.

1-2-1. Measurement

Figure 18:
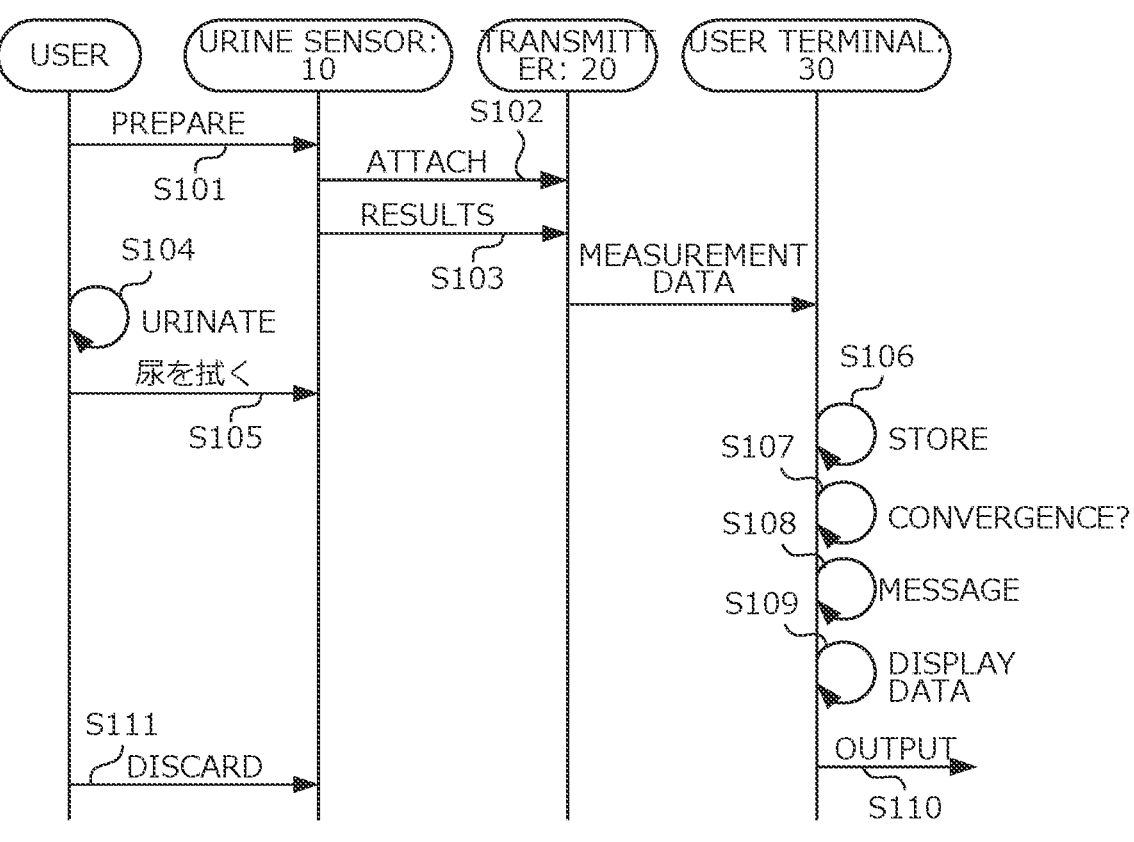
FIG. 18 is a sequence chart illustrating details of measurement processing.

FIG. 18 is a sequence chart illustrating details of the measurement process. Here, an example in which urine sensor 10 of FIG. 2 is used will be described. Transmitter 20 and user terminal 30 communicate using the Bluetooth protocol. The pairing between transmitter 20 and user terminal 30 is completed according to a predetermined procedure prior to the sequence of FIG. 18. In this instance, transmitter 20 is always powered on and transmitter 20 and user terminal 30 are in a state such that Bluetooth pairing is always established. Transmitter 20 and user terminal 30 are not always connected, and may be disconnected when the mode is shifted to the sleep mode or the like.

At step S101, the user prepares urine sensor 10. For example, urine sensor 10 is sold in singly in a package. A protective film is attached to sensor element 12. The user opens the package of urine sensor 10 and removes the protective film from sensor element 12. At step S102, the user attaches urine sensor 10 to transmitter 20. When urine sensor 10 is attached to transmitter 20, power is supplied from transmitter 20 to urine sensor 10. When power is supplied, urine sensor 10 outputs (at step S103) a signal indicative of results of measurements. Urine sensor 10 continuously outputs a signal while power is supplied. Transmitter 20 continues to transmit measurement data to user terminal 30 at regular time intervals while a pairing connection is established with user terminal 30. User terminal 30 continuously receives measurement data from transmitter 20 via this connection.

At step S104, the pet urinates. At step S105, when the pet urinates, sheet 15 of urine sensor 10 is exposed to the pet's urine. Sensor element 12 reacts upon exposure to the urine, and the output signal, e.g., the voltage value changes.

Figure 19:
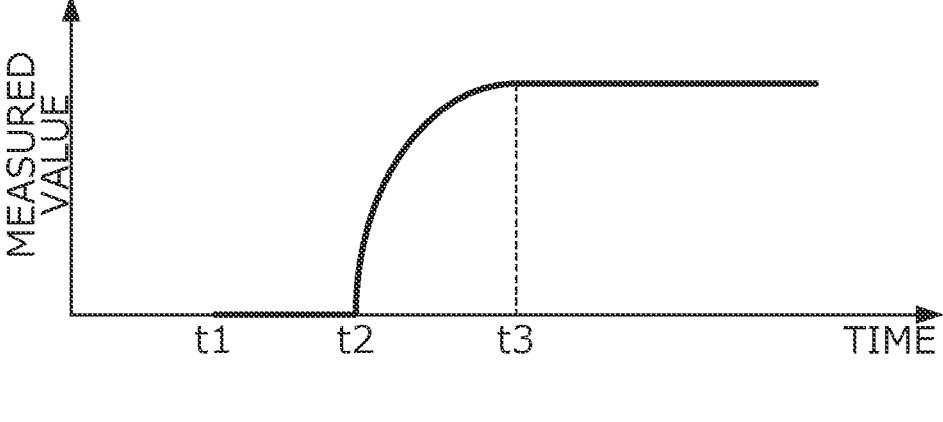
FIG. 19 is a diagram illustrating changes in measured values over time.

FIG. 19 is a diagram illustrating a temporal change in a measured value. The horizontal axis represents time, and the vertical axis represents measured values, for example, a concentration of specific components in urine. When urine sensor 10 is not attached, since the input terminal of input unit 21 is open, the voltage value is not measured, and a measured value is not obtained. At time t1, urine sensor 10 is attached to transmitter 20 and measurements start to be obtained. At this point, however, sensor element 12 is not in contact with the urine, and thus the measurement is close to zero. At time t2, the urine of the pet is applied to sheet 15, and the urine and sensor element 12 start to react with each other. The reaction proceeds at a certain time constant and finally converges.

Referring again to FIG. 18. At step S106, user terminal 30 stores the measured data received from transmitter 20 in storage unit 31. The control unit 36 determines (at step S107) whether the measured value indicated by the measured data satisfies a predetermined convergence condition. When it is determined that the convergence condition is satisfied, UI unit 37 displays (at step S108) a message indicating, for example, a successful measurement. Output unit 33 adds attribute data to the measurement data indicating the converged measurement value. The attribute data are data indicating the attributes of the measurement value, and in this example include a time stamp indicating the measured time and a user identifier identifying the user who is the owner of the pet that is a subject of measurement. Storage unit 31 stores the measurement data indicating the converged measurement data at step S109. Output unit 33 outputs the measured data to analyzing system 40 (step S110).

When the measurement data is output to analyzing system 40, UI unit 37 displays a message prompting the user to discard urine sensor 10. At this time, UI unit 37 may reproduce a moving image explaining how to discard urine sensor 10. The user removes urine sensor 10 from transmitter 20, and then peels sheet 15 from base 11 and flushes urine sensor 10 down a toilet. The user folds and discards (at step S111) base 11 from which the sheets 15 have been peeled.

According to the present embodiment, measurement of the urine can be performed, and the result can be recorded in association with urination of a pet. Urine sensor 10 is disposable and can be easily handled by a user.

1-2-2. Analysis

Figure 20:
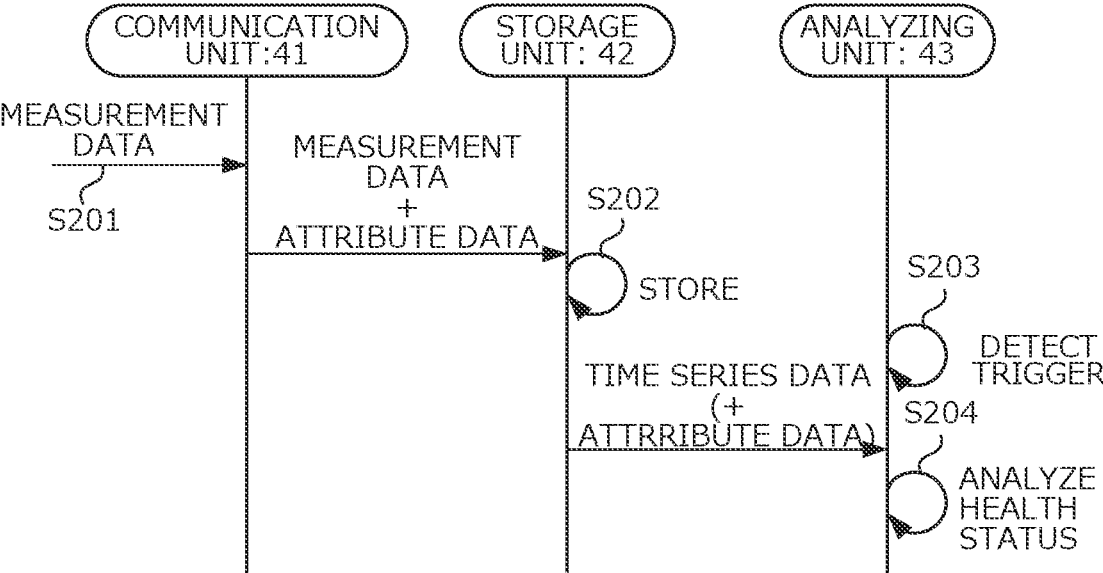
FIG. 20 is a sequence chart illustrating details of an analysis process.

FIG. 20 is a sequence chart illustrating details of the analysis process. At step S201, communication unit 41 of analyzing system 40 receives the measurement data from user terminal 30. At step S202, storage unit 42 stores the measurement data and the attribute data. In this example, since the attribute data includes the time stamp and the user identifier, when measurement data at a plurality of measurement timings is accumulated, storage unit 42 stores the detection result of specific components in the urine in a time series. Further, in this example, since urine sensor 10 detects a plurality of components in the urine, storage unit 42 can store detection results of a plurality of specific components in the urine in a time series.

Figure 21:
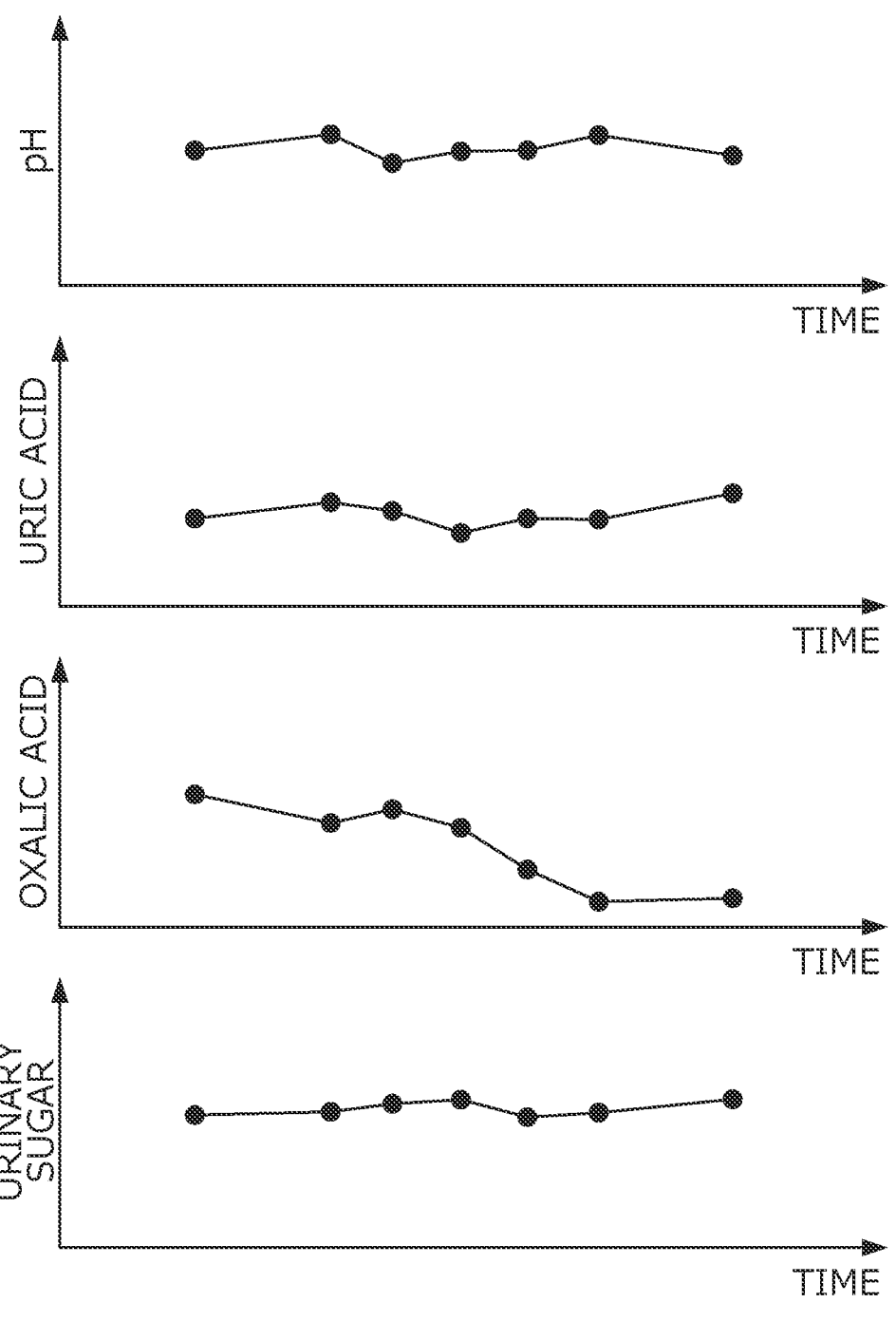
FIG. 21 is a diagram illustrating a time series of detection results.

FIG. 21 is a diagram illustrating a time series of detection results. In this example, pH, uric acid, oxalic acid, and urinary sugar values are detected in the urine. In the figure, the horizontal axis shows the date and time, and the vertical axis shows the measured values. For example, the measurement using urine sensor 10 is performed every time the pet urinates, and is performed on average four times a day. According to this example, a concentration of the four components in the urine over the specified time is recorded.

Referring again to FIG. 20. At step S203, analyzing unit 43 detects events that trigger analysis of a health condition of a user. The event includes a process in which analyzing system 40 receives a user identifier that identifies a user who is the owner of the pet for which a health condition is to be analyzed (hereinafter referred to as the "target user"). This event is, for example, an event in which the user instructs (notifies analyzing system 40) of the analysis of the health state in user terminal 30. Alternatively, the event may be an event where new measurement data is received from user terminal 30. Further alternatively, the event is an event in which a predetermined time has elapsed since the previous analysis of the health state of the target user. When the event that triggers analysis of a health state is detected, analyzing unit 43 shifts the process to step S204.

At step S204, analyzing unit 43 analyzes the health status of the pet of the target user specified by the user identifier. Time series data indicating the detection result of urine sensor 10 is used for analysis of the health state. When urine sensor 10 detects a plurality of components in the urine, analyzing unit 43 refers to the detection results of the plurality of components to comprehensively determine a health state of the target user.

The components measured by sensor element 12 are not limited to the above examples. Sensor element 12 detects, for example, at least one of the following components (1) to (12). The following measurement items and their interpretations are merely examples:

(1) pH: If urine is acidic, diabetes, cardiovascular disease, or alcoholism may be present. When urine is alkaline, a urinary tract infection or kidney disease may be present;

(2) Uric acid: Elevated uric acid levels may cause gout;

(3) Oxalate: High oxalate levels may indicate renal or ureteral stones;

(4) Urine sugar: Higher urine sugar (grade sugar) sugar levels may be a potential source of glucose. However, urine glucose levels fluctuate with diet, and so urine levels before breakfast should be measured;

(5) Protein: Higher protein concentrations may indicate reduced kidney function;

(6) Bilirubin: Bilirubin is the bile pigment of hemoglobin. High levels of bilirubin may indicate hepatic dysfunction or biliary obstruction;

(7) Urobilinogen: Urobilinogen results from degradation of bilirubin by intestinal bacteria. High levels of urobilinogen may cause damage to the liver or gallbladder;

(8) Specific gravity: Specific gravity of urine depends on components other than moisture, such as urea or sodium chloride. Low density may indicate renal failure, and high density may indicate diabetes mellitus or dehydration;

(9) Occult blood: High levels of occult blood may indicate abnormal kidneys, ureter, or bladder;

(10) Ketone bodies: Ketone bodies are intermediate metabolites during lipolysis. Higher concentrations of ketones may lead to diabetes, fever (cold or influenza), or excessive dieting;

(11) Nitrite: Nitrate in foods may be changed to nitrites by bacteria. High concentrations of nitrites may cause bladder or urinary tract infections; and

(12) Leukocyte: High levels of leukocyte may cause inflammation of the kidneys, bladder, prostate, or seminal vesicle glands.

2-3. Provision of Information

Figure 22:
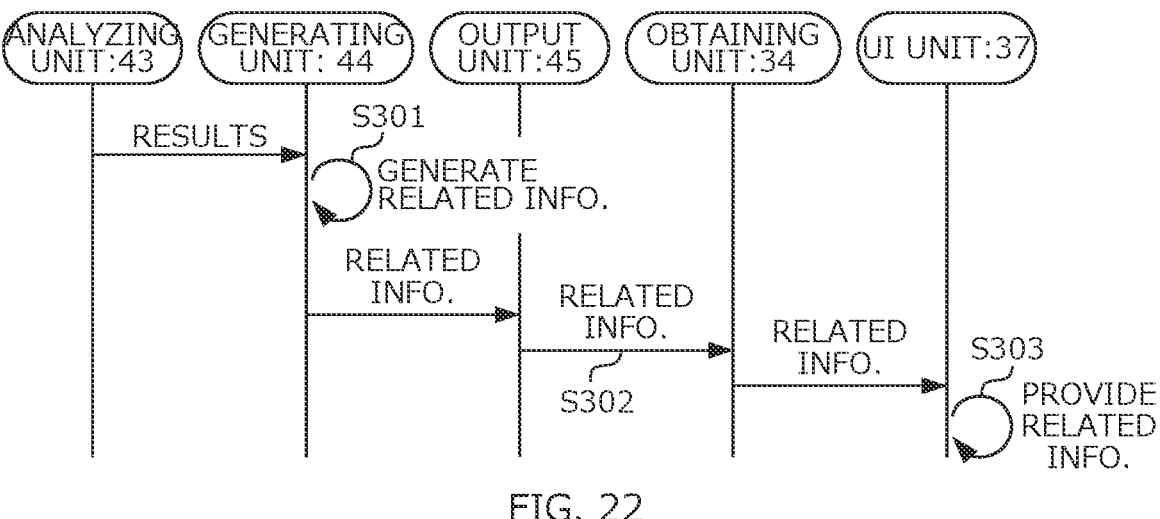
FIG. 22 is a diagram illustrating details of the information provision process.

FIG. 22 is a diagram illustrating details of information for providing processing. At step S301, generating unit 44 generates related information corresponding to the analysis result of a healthy state. As related information, for example, at least one of (1) information directly indicating an analysis result, (2) information obtained by interpreting the analysis result, (3) advice based on the analysis result, and (4) recommendation of a product related to the analysis result are used; and information provided as the related information is specified by, for example, a user who is a pet owner. Alternatively, analyzing system 40 may determine which information to provide as the related information depending on the analysis result. For example, when the analysis result indicates that there is no particular abnormality in the health state of the target user, analyzing system 40 provides information directly indicating the analysis result (for example, a graph of measurement data) and information obtained by interpreting the analysis result (for example, "no abnormality" display) as related information to user terminal 30. Alternatively, when the analysis result indicates a new abnormality (an abnormality not previously found) in the health state of the target user, analyzing system 40 provides information directly indicating the analysis result (e.g., a graph of measurement data), information obtained by interpreting the analysis result (e.g., suspected disease name), and advice based on the analysis result (e.g., introduction to a hospital where a specialist in the disease is present) to user terminal 30 as related information. Further alternatively, when the analysis result indicates an abnormality that is present chronically in the health state of the target user, analyzing system 40 provides information (for example, a deficient nutrient) obtained by interpreting the analysis result, and (4) recommendation of a commodity related to the analysis result (introduction of a supplement for ingestion of a nutrient) to user terminal 30 as related information. At step S302, the output unit 45 outputs the related information generated by generating unit 44 to user terminal 30 of the target user.

Obtaining unit 34 of user terminal 30 obtains related information from analyzing system 40. At step S303, UI unit 37 provides related information to the user. That is, UI unit 37 displays an image, a character string, a document, or a web page included in the related information, reproduces a moving image, or outputs sound.

According to this embodiment, it is possible to easily measure components in the urine of a pet, and further, it is possible to easily provide the user with information corresponding to the measurement result.

2. Second Embodiment

Figure 23:
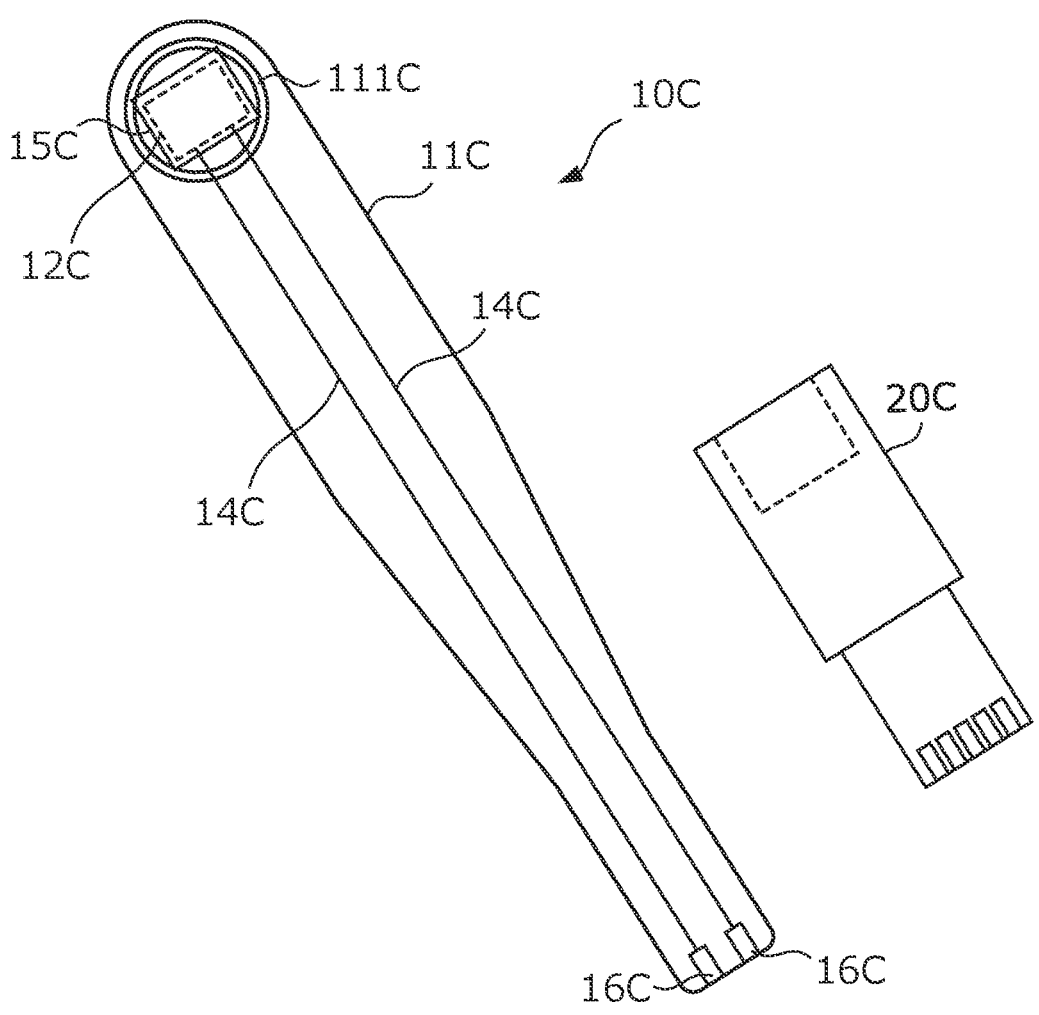
FIG. 23 is a diagram illustrating an appearance of Urinalysis device and Transmitter.

FIG. 23 is a diagram illustrating an external appearance of urinalysis device 10C and the external appearance of transmitter 20C according to the second embodiment. Urinalysis device 10C includes main body 11C, sensor device 12C, target 111C, signal line 14C, sheet 15C, and connecting terminal 16C. Body 11C has a longitudinal shape extending in one direction. Sensor element 12C outputs signals corresponding to particular components in urine. Signal line 14C transmits the output signal from sensor element 12C. Connecting terminal 16C is a terminal that connects signal line 14C to transmitter 20 (an example of an external device). Urinalysis device 10C can be applied to both human and animal subjects. If a human subject uses the urinalysis device 10C, the subject can hold transmitter 20C by hand and adjust its position so that the urine of the subject is applied to main body 11C. Transmitter 20C may be equipped with handles or grips or the like (not shown in the figures) to facilitate the handling by the user.

In the embodiment of FIG. 23, target 111C, sheet 15C, sensor element 12C, signal line 14C, and connection-terminal 16C are provided on body 11C. Main body 11C has a centrally provided longitudinal fold (not shown in the figures), which acts to guide urine applied to main body 11C to sheet 15C. Further, sheet 15C is provided at one end side of the center in the longitudinal direction in body 11C, and connecting terminal 16C is provided at the other end side in the longitudinal direction in body 11C.

While urinalysis device 10C is disposable, transmitter 20C is repeatedly used. Transmitter 20C has n input terminals like transmitter 20 described above, and signals corresponding to components in urine are outputted from transmitter 20C by signals inputted through the input terminal.

3. Modification

The present invention is not limited to the embodiments described above, and a variety of modifications can be made. Specific modifications described below are applicable to the embodiments described above. In addition, two or more of the following modified examples may be applied in combination. Further, at least a part of each of the embodiments and modifications may be combined with at least a part of other embodiments and modifications.

3-1. First Modification (Shape of Transmitter 20)

Figure 24:
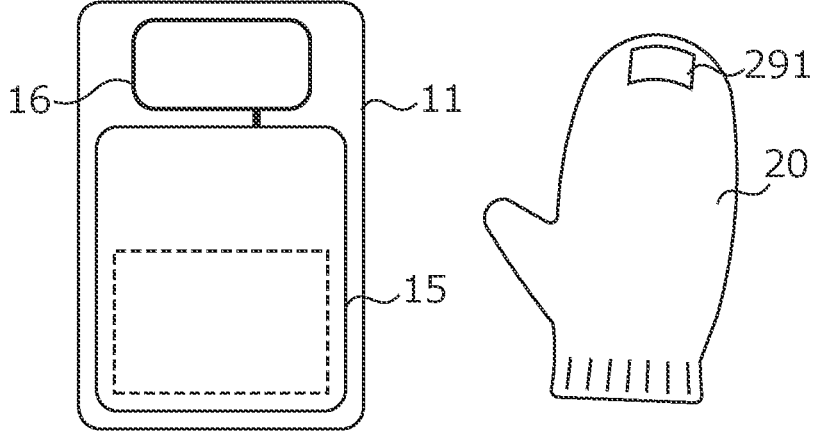
FIG. 24 is a diagram illustrating another example of transmitter 20.

FIG. 24 is a diagram showing another example of transmitter 20. The shape of transmitter 20 is not limited to that illustrated in FIG. 12. FIG. 24 shows an example in which transmitter 20 has a shape of a wearable device, more specifically a mitten, worn on a user's body. A wearable device is a device having a shape that can be worn by a user, e.g., a hat, glasses, watch, wristband, glove, shirt, pants, sock, or device embedded in a shoe. Although not shown in FIG. 24, a hardware element such as a CPU 201 is incorporated in a position corresponding to the back of a hand. In this example, transmitter 20 does not have a detachable mechanism 29, but instead has electrode 291, which is an example of a contact portion for forming an electrical connection with urine sensor 10, and is exposed on the surface of transmitter 20. Urine sensor 10 corresponding to this transmitter 20 also has, instead of or in addition to detachable mechanism 13, electrode 16 for forming an electrical connection with transmitter 20. Electrode 16 is exposed to base 11. Electrodes 291 and 16 are designed to be positioned, shaped, and sized to contact other when the user holds urine sensor 10 with transmitter 20 (glove) in place.

After the pet has urinated, the user places transmitter 20 (glove) in his/her hand. The user holds urine sensor 10 with a hand to which transmitter 20 is attached. In this state, an electrical connection between urine sensor 10 and transmitter 20 is formed, and an output signal from urine sensor 10 is transmitted to user terminal 30. The user then removes transmitter 20 and discards urine sensor 10. Transmitter 20 is reused.

3-2. Second Modification (Signal Transmission)

The transmission path of the signal from urine sensor 10 to transmitter 20 is not limited to that through the contact point between respective two electrodes. Non-contact signal transmission by electromagnetic induction may be used for transmission of signals from urine sensor 10 to transmitter 20. In this case, transmitter 20 includes a transmission unit (not shown in the figures) that performs non-contact signal transmission by electromagnetic induction with urine sensor 10.

Alternatively, transmitter 20 may be embedded in base 11 as a so-called non-contact IC card. In this case, transmitter 20 does not require a battery, and a circuit of transmitter 20 operates under induced electromotive force obtained by electromagnetic waves emitted from the reader/writer device. The reader/writer device is integrated, for example, in user terminal 30. Alternatively, the reader/writer device may be provided as an external device connected to user terminal 30. In this case, transmitter 20 may be non-detachable from base 11 and may be discarded as waste for incineration with base 11 or to be flushed down a toilet.

3-3. Third Modification (Mounting/Dismounting Mechanism)

In urine sensor 10 and transmitter 20, specific examples of detachable mechanism 13 and the detachable mechanism 29 are not limited to those exemplified in the embodiment. In the embodiment, an example in which detachable mechanism 13 and detachable mechanism 29 are formed by snap fitting has been described, but detachable mechanism 13 and the detachable mechanism 29 may be formed by using a surface fastener utilizing a conductive material.

3-4. Fourth Modification (Data)

Data output from user terminal 30 to analyzing system 40 are not limited to measurement data. Data other than the measurement data may be output to analyzing system 40 as long as the information is used to determine a health condition of a pet. Other data are, for example, data containing information about food and drink consumed by the pet (hereinafter referred to as "food and drink data"). The information on the food and drink is, for example, information specifying a time when the food and drink is ingested, the name of the ingested food and drink, and the amount of the ingested food and drink. Alternatively, the other data may be data including information relating to exercise performed by the pet, e.g., information specifying the intensity of the exercise and the exercise time. Still alternatively, the other information may include attributes of the pet, such as age, sex, and history. Upon provision of these data, analyzing system 40 analyzes the health of the pet taking the data into account in addition to the measured data. That is, generating unit 44 generates the related information according to the measurement data and the food and drink data.

The food and beverage data may include, for example, a photograph of a meal. When the pet takes a meal, the user takes a picture of the meal at user terminal 30. User terminal 30 includes a camera (not shown in the figures) for taking pictures. User terminal 30 outputs a photograph of the dish to analyzing system 40. The photograph is time-stamped, and the time stamp is used to obtain a time of consumption of food and drink. Analyzing system 40 accesses AI that analyzes the photograph of the food to determine calories and nutrients, and obtains information indicating the calories and nutrients of the meal taken by the pet.

In one example, health support system 1 may be used to demonstrate an effect of a functional food or health supplement (hereinafter referred to as "health food"). For example, juices of certain green vegetables are known to have the effect of rendering alkalinity. According to health support system 1 of the present embodiment, the effects of these health foods can be verified.

Figure 25:
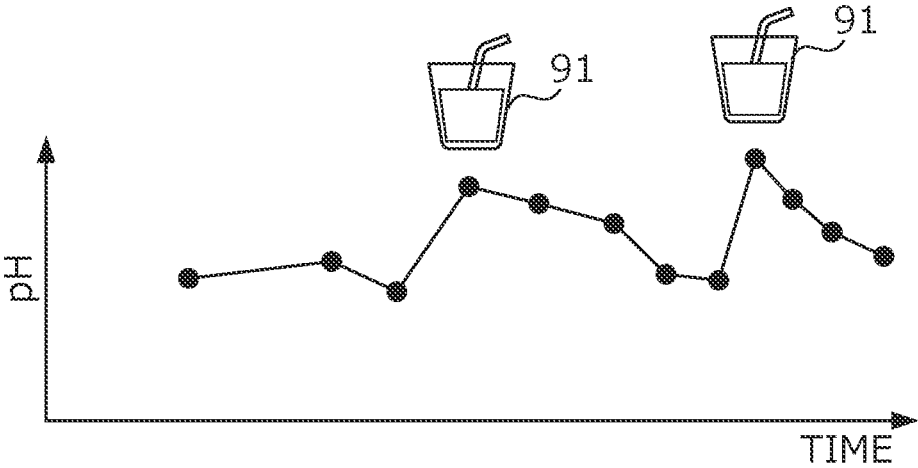
FIG. 25 is a diagram illustrating effects of health foods.

FIG. 25 is a diagram illustrating a demonstration of the effect of a health food. FIG. 25 is a diagram illustrating an example of a UI screen in user terminal 30. This screen contains a graph showing a time course of ingredients (e.g., pH) associated with health food. In addition, the timing of ingestion of the health food is shown on the graph. In this example, icon 91 is shown at a position corresponding to the time of ingestion of the health food. In the example shown, the urine changes to alkaline immediately after ingestion of the health food, and then gradually becomes more acidic. According to this example, it is possible to visually represent the effect of the ingestion of the health food. This system can be used to improve the motivation of pet health maintenance and disease prevention, as well as to promote the sale of health foods.

3-5. Fifth Modification (for Common Use of Transmitters)

In an embodiment, one transmitter 20 was dedicated to a particular user. However, one transmitter 20 may be shared by a plurality of users or pets. In this case, transmitter 20 has a plurality of storage areas corresponding to different identifiers or users. That is, each storage area is set to a separate identifier. One identifier is used by one pet. For example, if storage unit 23 has four identifiers (four storage areas), transmitter 20 can be shared by a maximum of four pets. In this example, transmitter 20 further includes a receiving unit (not shown in the figures). The receiving unit accepts one of a plurality of identifiers. The receiving unit is a type of UI, and is, for example, a switch. Storage unit 23 stores the measurement data in the storage area corresponding to one identifier designated through the reception unit among the plurality of storage areas. Wireless communication unit 24 transmits the data stored in the storage area corresponding to the one identifier specified via the receiving unit and the wireless signal indicating the one identifier. For example, if the owner of each of these four pets has a unique user terminal 30, transmitter 20 establishes a connection with user terminal 30 corresponding to the pet specified by the receiving unit among these four user terminals 30.

In a case where one transmitter 20 is shared by a plurality of pets, transmitter 20 may not have a plurality of storage areas corresponding to the plurality of pets. In this case, for example, user terminal 30 is shared by a plurality of pets. User terminal 30 switches pets by a so-called login process. User terminal 30 appends the identifier of the logged-in pet to the measurement data.

3-6. Sixth Modification (Encryption)

Transmitter 20 may encrypt the measurement data when transmitting the measurement data to user terminal 30. In this case, transmitter 20 and user terminal 30 exchange an encryption key prior to transmission and reception of the measurement data. In one example, user terminal 30 transmits the encryption key to transmitter 20. Transmitter 20 encrypts the data using the encryption key and then transmits the measurement data to user terminal 30. User terminal 30 decrypts the measurement data using the encryption key transmitted to transmitter 20 and the corresponding decryption key. Since measurement data constitutes a form of personal information, a security risk exists if such information is transmitted as plaintext. This risk is obviated by encryption.

3-7. Seventh Modification (Convergence Condition)

The convergence conditions for determining whether the measured value obtained from urine sensor 10 has converged are not limited to those exemplified in the embodiment. For example, the provider of urine sensor 10 confirms the time τ until the measured value converges in urine sensor 10 in advance by experiment. The provider of urine sensor 10 sets the value of the time τ in the client program. The control unit 36 of user terminal 30, when the elapsed time from the time when the measurement value starts to be obtained (e.g., time t2 in FIG. 17) exceeds τ, the measured value may be determined to have converged. Alternatively, user terminal 30 may output the measurement data to analyzing system 40 at predetermined time intervals after the time when the measurement value starts to be obtained without determining whether the measurement value has converged, and analyzing system 40 may determine whether the measurement value has converged. If it is determined that the measured value has converged, analyzing system 40 notifies user terminal 30 of the convergence. Upon receiving the notification, user terminal 30 stops outputting the measurement data.

3-8. Eighth Modification (Time Division Processing)

The output signal from the plurality of sensor elements 12 in the embodiment has been described as an example in which transmitter 20 wirelessly transmits to user terminal 30 in time division. Even if urine sensor 10 has a plurality of sensor elements 12, transmitter 20 may not transmit the output signals from all the sensor elements 12 in time division. For example, transmitter 20, among the plurality of sensor elements 12, outputs only the output signal from sensor element 12 of a portion selected by the user (e.g., one). In this case, transmitter 20 may have a UI element (e.g., a switch) for selecting sensor element 12 of interest. Alternatively, the user may select target sensor element 12 at user terminal 30, and user terminal 30 may transmit information to transmitter 20 identifying the target sensor element 12. Transmitter 20, among the plurality of sensor elements 12, outputs only the output signal of (a portion of) sensor element 12 selected by the user in time division (when a single sensor element 12 is selected outputs only the output signal of sensor element 12 without time division).

In another example, urine sensor 10, rather than transmitter 20, may have time-sharing processing capabilities. In this case, urine sensor 10 has a circuit corresponding to selecting circuit 222. Urine sensor 10 outputs a signal in which the output signals from the plurality of sensor elements 12 are time-division multiplexed to transmitter 20. According to this example, the number of output terminals and input terminals that transmits signals from urine sensor 10 to transmitter 20 can be reduced.

3-9. Ninth Modification (Combination of Measurement Items)

A provider of urine sensors 10 may combine different types of sensor elements 12 in providing urine sensor 10 having a plurality of sensor elements 12. For example, in providing urine sensor 10 having four sensor elements 12, sensor elements 12A-D may measure pH, uric acid, oxalic acid, and urine sugar in one product (hereinafter referred to as urine sensor 10A), and sensor elements 12A-D may measure specific gravity, occult blood, ketones, and nitrites in another product (hereinafter referred to as urine sensor 10B). The provider of urine sensor 10 assigns an identification code to a combination of sensor elements 12. The identification code may be, for example, a string (e.g., an identification number) or an image (e.g., a so-called two-dimensional bar code). This identification code is provided, for example, on a surface of base 11 or in the package of urine sensor 10. The user enters an identification code, e.g., as provided on base 11 or in the package, into user terminal 30. User terminal 30 has information to convert the identification code into a combination of measurement items, which for example, are acquired from analyzing system 40, and refers to this information to determine which sensor element 12 output signal indicates which measurement item result. According to this example, it is possible to provide urine sensor 10 with a variety of combinations of measurement items.

3-10. Tenth Modification (Sharing of Processing)

The sharing of processing in each device is not limited to those described in the embodiments. For example, at least a portion of the processing performed in analyzing system 40 in the embodiment may be performed by user terminal 30. As an example, storage unit 31 of user terminal 30 may store the measurement data in time series. Control unit 36 generates time-series data using the time-series measurement data stored in storage unit 31, or the control unit 36 performs statistical processing on the time-series measurement data and generates statistically processed measurement data. User terminal 30 outputs the generated data to analyzing system 40.

In another example, even when user terminal 30 outputs the measurement data to analyzing system 40, storage unit 31 of user terminal 30 may store the same data as that output to analyzing system 40. In particular, when analyzing system 40 is implemented in a so-called cloud, if the measurement data is stored in storage unit 31, some processing such as confirmation of measurement data and statistical processing can be performed locally (without need to connect to a network).

3-11. Eleventh Modification (Shape of Substrate)

The shape and material of base 11 are not limited to those illustrated in the embodiments. For example, base 11 may be a diaper worn by a subject.

Figure 26:
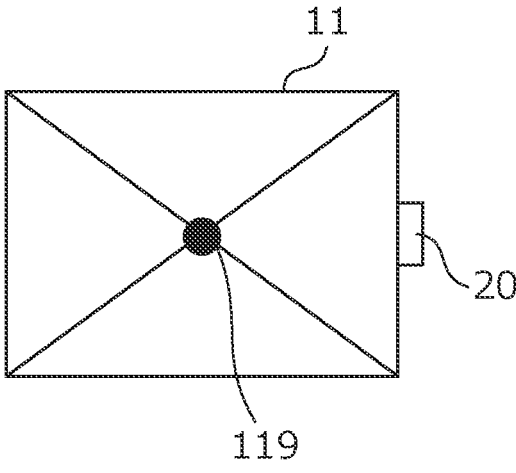
FIG. 26 is a diagram illustrating still another example of the configuration of urine sensor 10.
Figure 27:
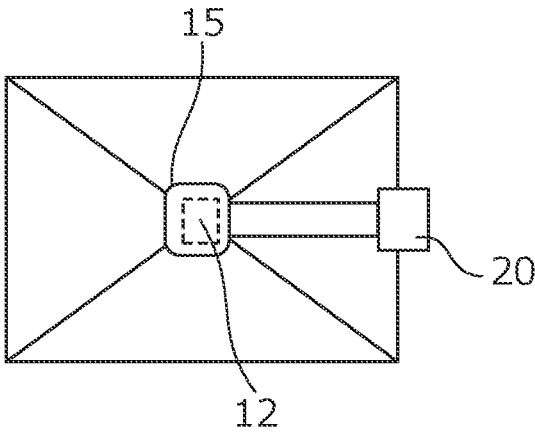
FIG. 27 is a diagram illustrating still another example of the configuration of urine sensor 10.
Figure 28:
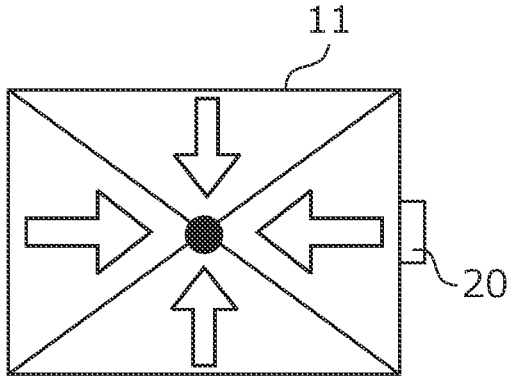
FIG. 28 is a diagram illustrating still another example of the configuration of urine sensor 10.

FIGS. 26-28 are views illustrating another example of urine sensor 10 exemplified in FIGS. 6-8 (i.e., a pet toilet sheet). FIG. 26 is a top view of base 11 used in urine sensor 10 of this example in a use state. In this example, base 11 has a surface structure in which the periphery of the depression rises at the center. That is, in the use state, the center is low and the periphery is high. Base 11 has through-hole 119 in the center (or at a point of center of gravity). FIG. 27 is a bottom view of base 11 in use. Sheet 15 and sensor element 12 are attached to the bottom surface of base 11. Sensor element 12 and transmitter 20 are connected by wiring. Transmitter 20 may or may not be fixed to base 11, and box 116 may be provided with a recess and placed or fitted in the recess. According to this example, as shown in FIG. 28 the pet's urine can be more efficiently collected in sensor element 12. Also in the examples of FIGS. 6 to 8, sensor element 12 may not be disposed on the top surface of base 11 and may be disposed on the bottom surface side, that is, on the back surface. In this case, a hole is provided at a position corresponding to sensor element 12 to guide urine to sensor element 12.

3-12. Twelfth Modification (Assisting Mechanism)

Urine sensor 10 may include an assisting mechanism (not shown in the figures) that assists in directing urine deposited on base 11 to sensor element 12. The assisting mechanism may include, for example, a mechanism for vibrating base 11, for example, a vibrator device for vibrating the piezo-electric element. The auxiliary device may include a sensor for detecting a movement associated with the subject urinating relative to base 11, e.g., the subject approaching urine sensor 10 or touching urine sensor 10, and the auxiliary device may operate based on a signal from the sensor.

3-13. Modification 13 (Fixed Part)

In the embodiments described above, detachable mechanism 13 and the detachable mechanism 18 may be integrally formed. In this case, detachable mechanism 13 has a signal line that transmits the output signal from sensor element 12, and a connecting terminal that connects the signal line to the external device (transmitter 20).

3-14. Other Modifications

Although an example in which urine is measured has been described in the above embodiment, the target of measurement is not limited to urine. The health support system according to the present invention may be used to measure body fluids other than urine, such as sweat, saliva, or blood.

The specific hardware configuration of each element constituting the health support system according to the above embodiment is not limited to that exemplified in the embodiment. Each element may have a different hardware configuration.

The invention claimed is:

1. A urinalysis device, comprising:
a target on which a subject urinates, the target being formed of a water-repellent material;
an absorbent portion formed of a water-absorbing material and at least partially in contact with the target;
a surface structure of the target that forms a pathway for directing urine for application to the absorbent portion;
a sensor element that is provided in the absorbent portion and outputs signals corresponding to components in the urine;
a body having a sheet shape; and
a box having an opening at least in a part other than a bottom surface, wherein
the absorbing portion and the sensor element are provided in the body,
the body is placed on the bottom surface, and
the bottom surface is inclined such that, in the installed state of the body, a part corresponding to the absorbing portion is low and a part corresponding to the target is high.

2. The urinalysis device according to claim 1, further comprising
a support plate fixed to an upper side of the body in the box and having at least one through-hole formed therein.

3. The urinalysis device according to claim 2, wherein the box and the support plate are formed from paper.

4. A health support system comprising:
the urinalysis device according to claim 1;
a transmitter connected to the sensor element; and
a user terminal used by a user, wherein
the transmitter includes
an input unit to which an output signal of the sensor element is input,
a storage unit that stores an identifier of the transmitter, and
a wireless communication unit that transmits data corresponding to the output signal and a wireless signal indicating the identifier,
the user terminal includes,
a storage unit that stores an identifier corresponding to the user,
a wireless receiving unit that receives the wireless signal from the transmitter,
an output unit that outputs the data to an analyzing system for analyzing a health condition of the user based on a specific component indicated by the data when the identifier indicated by the wireless signal matches the identifier stored in the storage unit, and
an obtaining unit that obtains information corresponding to a result of an analysis from the analyzing system.

* * * * *